(12) United States Patent
Fukasawa et al.

(10) Patent No.: US 10,478,059 B2
(45) Date of Patent: Nov. 19, 2019

(54) IMAGING APPARATUS

(71) Applicant: CANON KABUSHIKI KAISHA, Tokyo (JP)

(72) Inventors: Taro Fukasawa, Fuchu (JP); Toshiharu Sumiya, Hiratsuka (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 82 days.

(21) Appl. No.: 15/570,530

(22) PCT Filed: Mar. 30, 2016

(86) PCT No.: PCT/JP2016/001840
§ 371 (c)(1),
(2) Date: Oct. 30, 2017

(87) PCT Pub. No.: WO2016/178298
PCT Pub. Date: Nov. 10, 2016

(65) Prior Publication Data
US 2018/0140183 A1 May 24, 2018

(30) Foreign Application Priority Data

May 1, 2015 (JP) .................................. 2015-094340
Sep. 4, 2015 (JP) .................................. 2015-175019

(51) Int. Cl.
*A61B 3/10* (2006.01)
*A61B 3/12* (2006.01)
(Continued)

(52) U.S. Cl.
CPC ............ *A61B 3/102* (2013.01); *A61B 3/1225* (2013.01); *A61B 5/0066* (2013.01);
(Continued)

(58) Field of Classification Search
CPC ..... A61B 3/102; A61B 3/1225; A61B 5/0066; G01B 9/02004; G01B 9/02069; G01B 9/02091; G01B 2290/65
See application file for complete search history.

(56) References Cited

U.S. PATENT DOCUMENTS 8,690,330 B2 * 4/2014 Hacker .................. A61B 3/102
351/221
2003/0103212 A1 6/2003 Westphal
(Continued)

FOREIGN PATENT DOCUMENTS

JP 2012-115578 A 6/2012

OTHER PUBLICATIONS

Chen D. Lu, et al., Handheld Ultrahigh Speed Swept Source Optical Coherence Tomography Instrument Using a MEMS Scanning Mirror, Biomedical Optics Express, Jan. 1, 2014, vol. 5, No. pp. 293-311.
(Continued)

*Primary Examiner* — Michael A Lyons
(74) *Attorney, Agent, or Firm* — Canon U.S.A., Inc. IP Division

(57) ABSTRACT

An SS-OCT apparatus includes a clock generator configured as an interferometer including an optical path through which part of light emitted from a light source passes, the optical path being split into a first optical path and a second optical path having an optical path length difference relative to the first optical path, to generate a clock used by a converter sampling an analog signal; a tomographic image obtaining unit configured to obtain a tomographic image of a fundus by using a digital signal converted from the analog signal sampled by the converter using the generated clock; and a scan unit configured to scan illumination light across the fundus at a scan angle of 47 degrees or more in air. The tomographic image obtaining unit is configured to obtain a
(Continued)

tomographic image of the fundus at a distance of 4.0 mm more within an eyeball in a depth range.

28 Claims, 8 Drawing Sheets

(51) Int. Cl.
*A61B 5/00* (2006.01)
*G01B 9/02* (2006.01)

(52) U.S. Cl.
CPC ..... *G01B 9/02004* (2013.01); *G01B 9/02069* (2013.01); *G01B 9/02091* (2013.01); *G01B 9/02067* (2013.01); *G01B 2290/65* (2013.01)

(56) References Cited

U.S. PATENT DOCUMENTS

| | | | |
|---|---|---|---|
| 2008/0291463 A1 | 11/2008 | Milner | |
| 2009/0046295 A1 | 2/2009 | Kemp | |
| 2011/0255095 A1 | 10/2011 | Jiang | |
| 2014/0160488 A1 | 6/2014 | Zhou | |
| 2014/0176963 A1* | 6/2014 | Kemp | G01B 9/02004 356/497 |
| 2014/0368827 A1* | 12/2014 | Fujii | G01B 9/02091 356/479 |
| 2015/0204651 A1* | 7/2015 | Yuan | G01B 9/02075 356/479 |
| 2015/0241202 A1* | 8/2015 | Jiang | G01B 9/02091 356/479 |
| 2016/0069664 A1* | 3/2016 | Yamanari | G01B 9/02091 356/479 |
| 2016/0084715 A1* | 3/2016 | Hori | G01B 9/02004 356/479 |
| 2017/0065169 A1* | 3/2017 | Fukasawa | A61B 3/102 |
| 2017/0127937 A1* | 5/2017 | Fujii | G01B 9/02004 |

OTHER PUBLICATIONS

Zhao Wang, et al., Depth-Encoded All-Fiber Swept Source Polarization Sensitive OCT, Biomedical Optics Express, Sep. 1, 2014, vol. 5, No. 9 pp. 2931-2949.

Ireneusz Grulkowski et al.; " Retinal, Anterior Segment and Full Eye Imaging Using Ultrahigh Speed Swept Source OCT with Vertical-Cavity Surface Emitting Lasers;" BioMedical Optics Express 2733, Nov. 1, 2012, vol. 3, No. 11; pp. 1-19.

* cited by examiner

[Fig. 1]
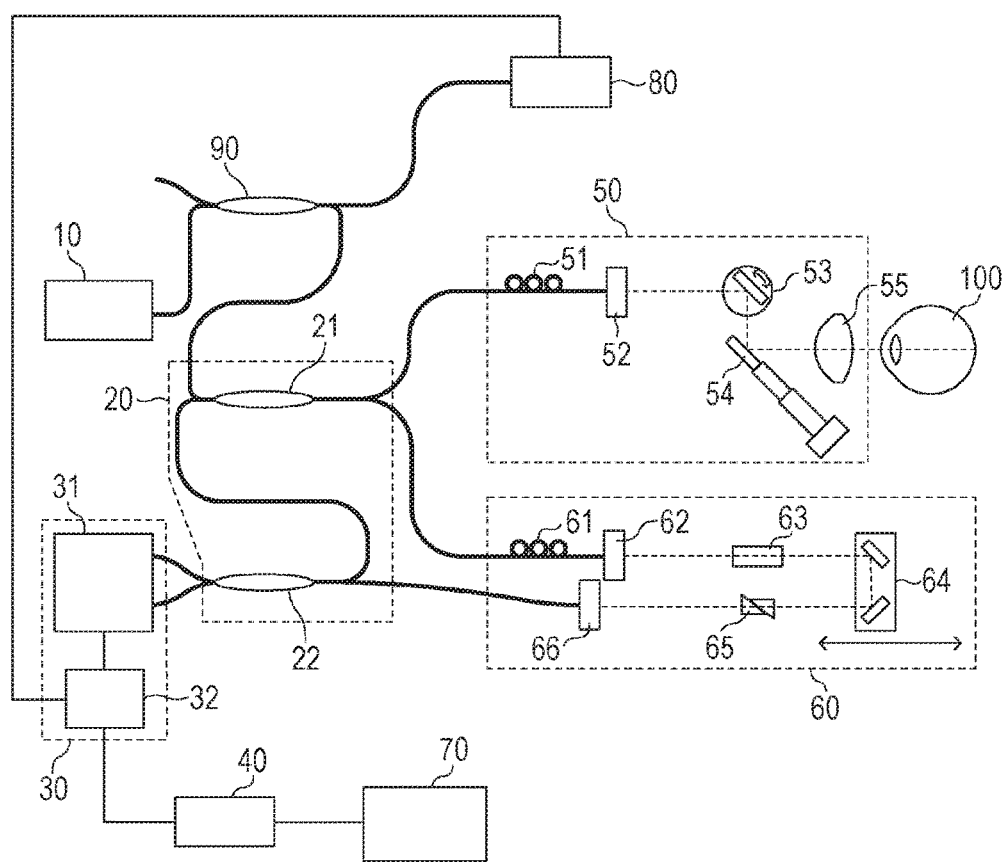

[Fig. 2A]
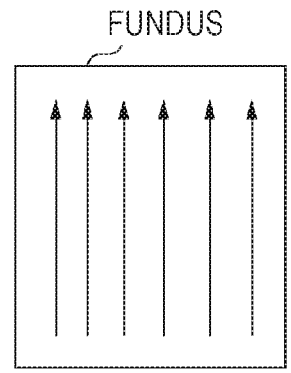
[Fig. 2B]
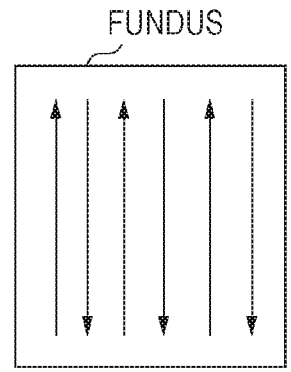
[Fig. 2C]
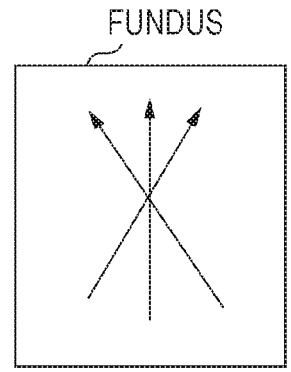

[Fig. 2D]
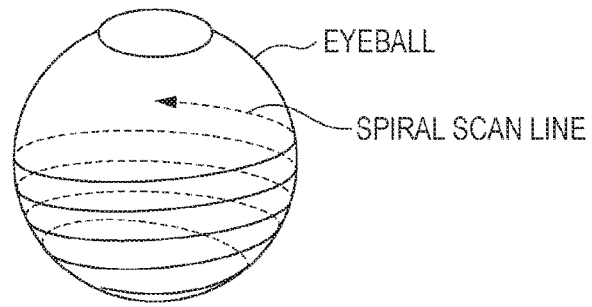
[Fig. 3]
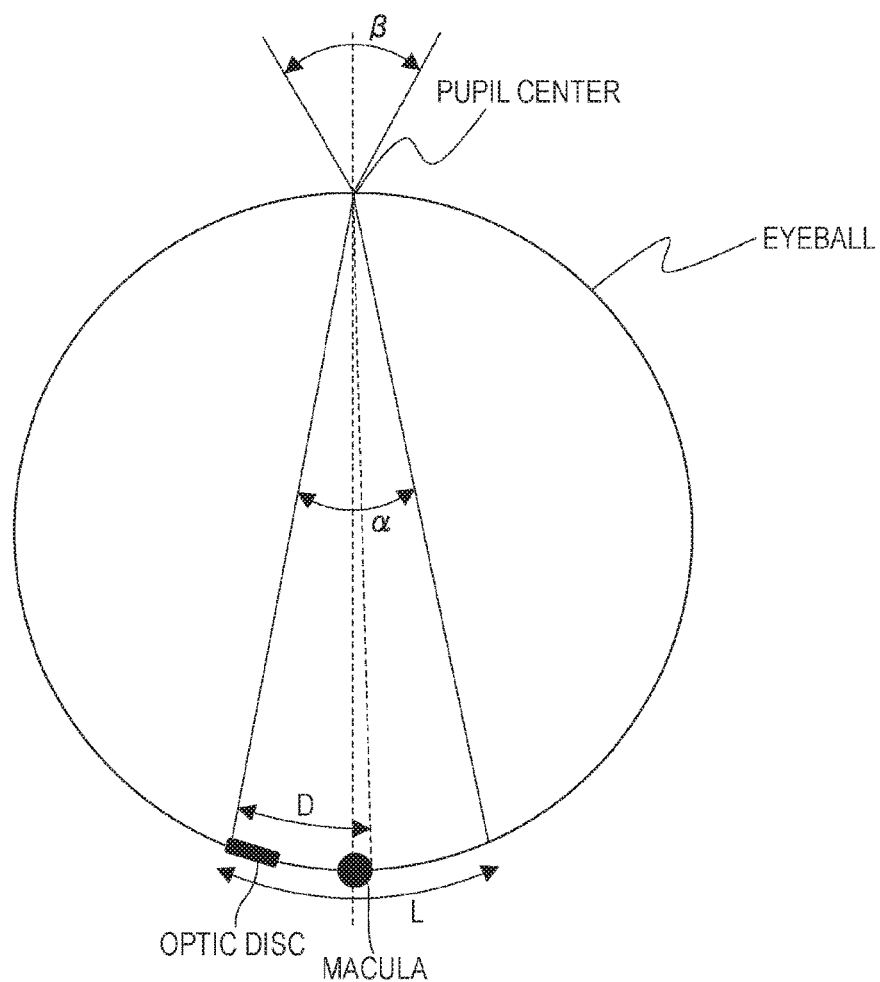

[Fig. 4]
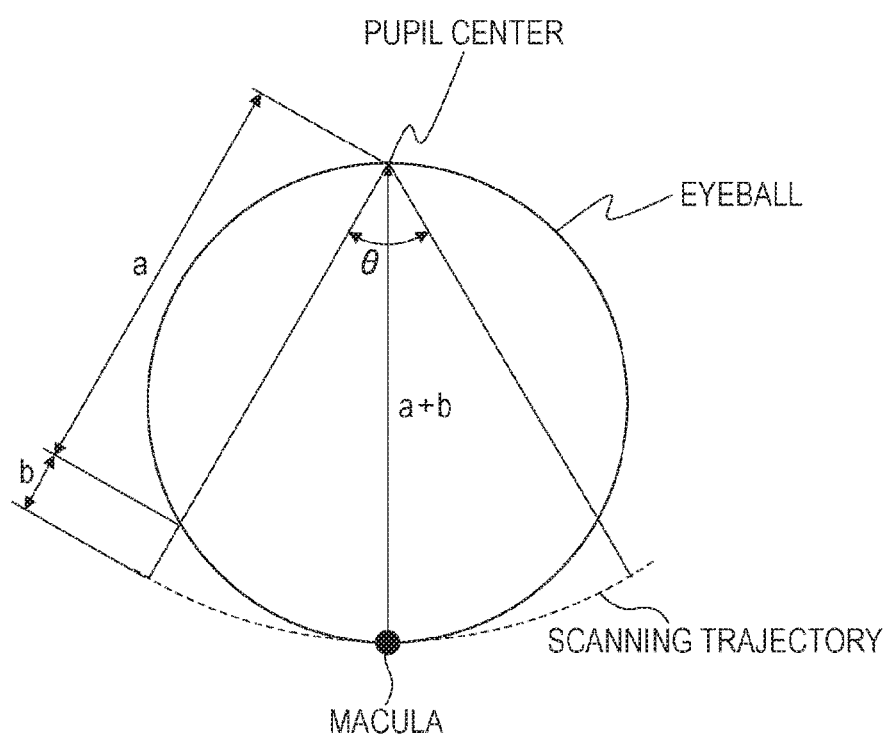

[Fig. 5A]
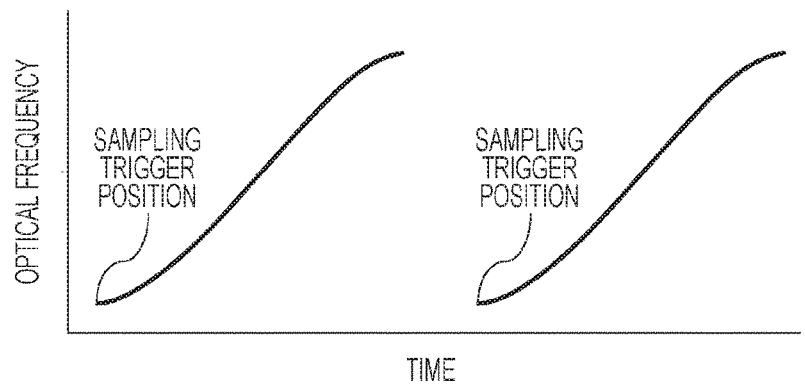
[Fig. 5B]
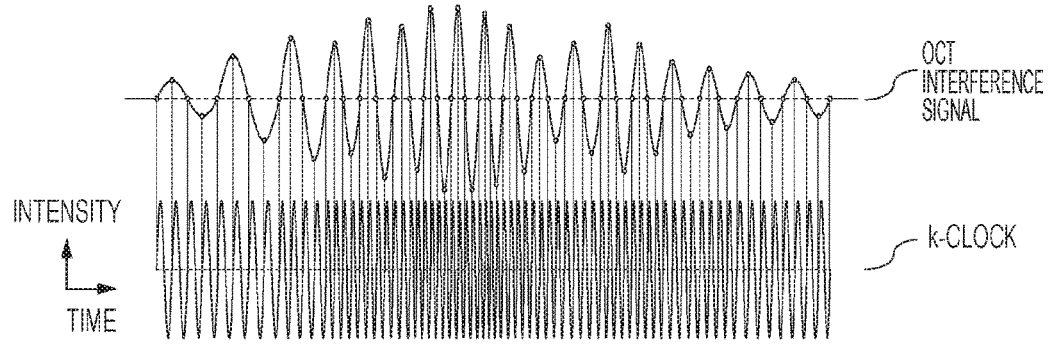

[Fig. 6]
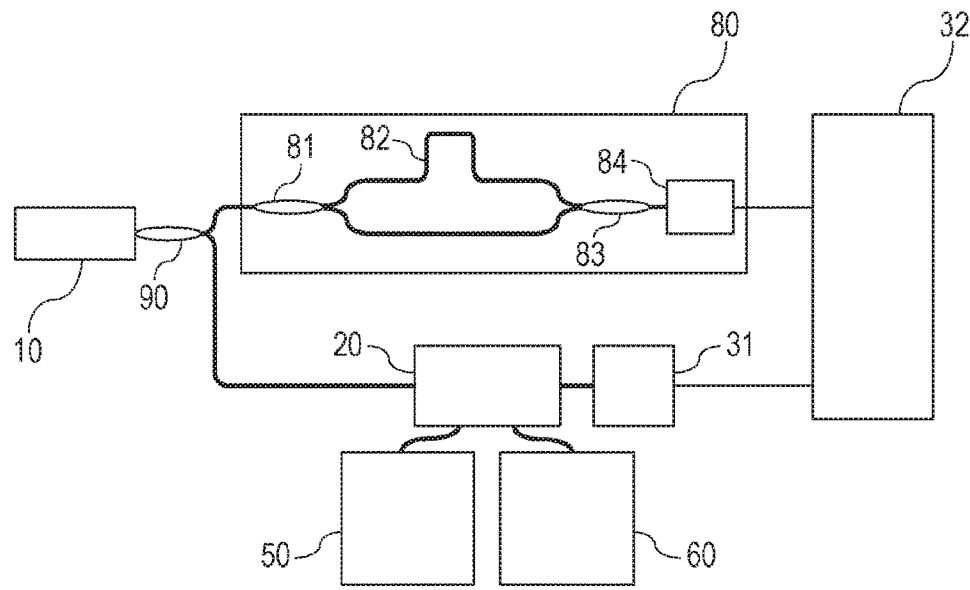
[Fig. 7A]
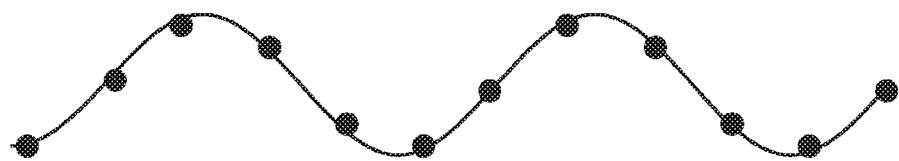
[Fig. 7B]
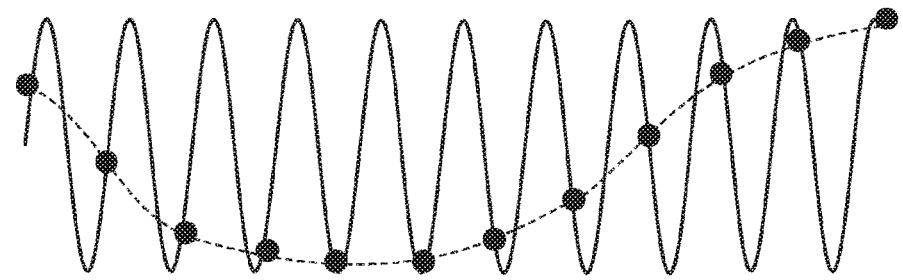

[Fig. 8]
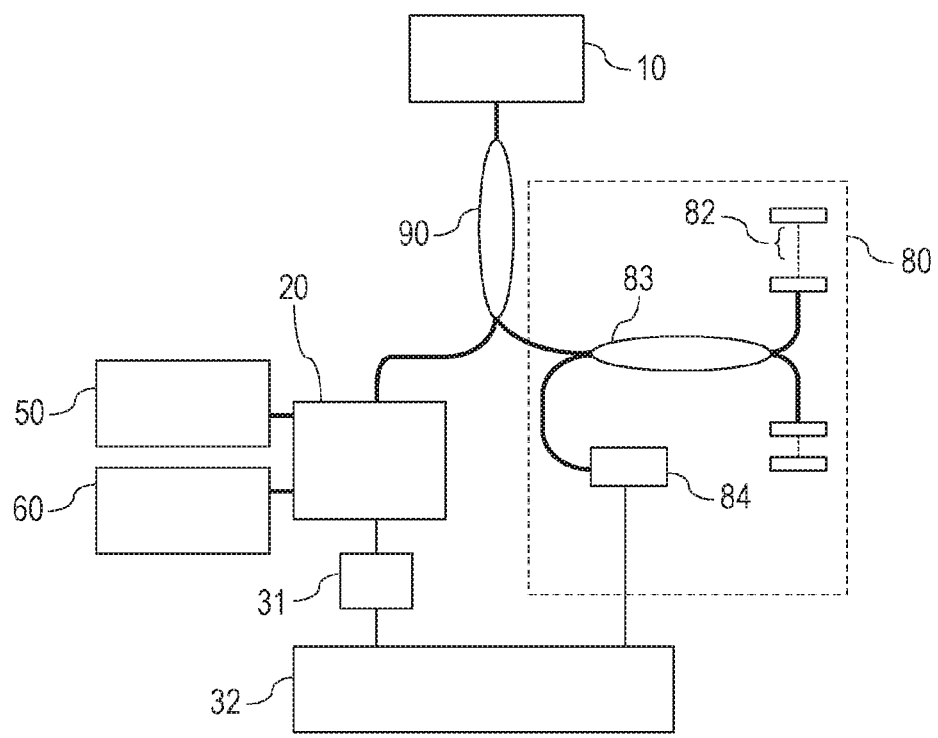

[Fig. 9]

| | | DEPTH RANGE OF TOMOGRAPHIC IMAGE (mm) | | NUMBER OF SAMPLES N (NUMBER OF TIMES) | CLOCK FREQUENCY fs (MHz) | k-CLOCK INTERFEROMETER (n IS AN INTEGER EQUAL TO OR LARGER THAN 1) | | |
|---|---|---|---|---|---|---|---|---|
| | | WITHIN EYEBALL | IN AIR | | | SINGLE PATH OR DOUBLE PATH | OPTICAL PATH LENGTH DIFFERENCE (mm) | FREQUENCY fk (MHz) |
| RELATED ART | | 2.6 | 3.6 | 1464 | 328.25 | SINGLE PATH | 14.4/n | 328.25/n |
| | | | | | | DOUBLE PATH | 7.2/n | |
| PRESENT EMBODIMENT | (a) | 4.0 | 5.5 | 2237 | 501.57 | SINGLE PATH | 22/n | 501.57/n |
| | | | | | | DOUBLE PATH | 11/n | |
| | (b) | 5.0 | 6.9 | 2807 | 629.37 | SINGLE PATH | 27.6/n | 629.37/n |
| | | | | | | DOUBLE PATH | 13.8/n | |
| | (c) | 5.8 | 8 | 3254 | 729.6 | SINGLE PATH | 32/n | 729.6/n |
| | | | | | | DOUBLE PATH | 16/n | |

IMAGING APPARATUS

TECHNICAL FIELD

The present invention relates to an imaging apparatus that captures optical coherence tomographic images.

BACKGROUND ART

Imaging apparatuses that employ optical coherence tomography (hereinafter referred to as OCT) are being developed (see PTL 1) (hereinafter, an imaging apparatus that employs OCT is referred to as an OCT apparatus). An OCT apparatus illuminates an object with light while changing the wavelength of the illumination light and makes reflection light beams returned from different depths of the object interfere with reference light to generate interference light. Then, frequency components of the temporal waveform representing the intensity of the interference light are analyzed to thereby obtain a tomographic image of the object. An OCT apparatus is used in fundus examinations, for example.

A large number of ocular diseases are difficult to completely cure. Therefore, it is important to find any lesion in the fundus earlier and to start a treatment that slows the spreading of the lesion over a wide area of the fundus earlier. Particularly, if the lesion reaches the macula, vision is seriously impaired. Therefore, it is desirable to find any lesion even if the lesion is located sufficiently away from the macula. To meet such a desire, an OCT apparatus used in fundus examinations is expected to have a wider angle of view.

PTL 1 discloses a technique for creating a tomographic image of a wide area by combining together a plurality of tomographic images in order to widen the area of the fundus which is observable on the tomographic image. PTL 1 also discloses an OCT apparatus that employs a swept light source (a swept-source OCT apparatus, hereinafter referred to as an SS-OCT apparatus). According to PTL 1, the swept light source is constituted by a fiber-ring resonator and a wavelength-selective filter, for example.

CITATION LIST

Patent Literature

PTL 1: Japanese Patent Laid-Open No. 2012-115578

Non Patent Literature

NPL 1: Depth-encoded all-fiber swept source polarization sensitive OCT (1 Sep. 2014_Vol. 5, No. 9 BIOMEDICAL OPTICS EXPRESS)

SUMMARY OF INVENTION

Solution to Problem

The present invention provides an imaging apparatus including a light source, an interference unit, a scan unit, a detector, a converter, a clock generator, and a tomographic image obtaining unit. The light source is configured to emit light while sweeping a wavelength of the light. The interference unit is configured to split the light emitted from the light source into illumination light that is incident on a fundus and reference light and to generate interference light obtained by reflection light reflected from the fundus on which the illumination light is incident interfering with the reference light. The scan unit is configured to scan the illumination light across the fundus. The detector is configured to detect the interference light generated by the interference unit. The converter is configured to convert an analog signal generated from the interference light detected by the detector into a digital signal. The clock generator is configured as an interferometer including an optical path through which part of the light emitted from the light source passes, the optical path being split into a first optical path and a second optical path having an optical path length difference relative to the first optical path, to generate a clock used by the converter sampling the analog signal. The tomographic image obtaining unit is configured to obtain a tomographic image of the fundus by using the digital signal converted from the analog signal sampled by the converter in accordance with the generated clock. The scan unit is configured to scan the illumination light across the fundus over a scan angle equal to or larger than 47 degrees in air. The tomographic image obtaining unit is configured to obtain a tomographic image of the fundus at a distance equal to or larger than 4.0 mm within an eyeball in a depth range. The clock generator is configured so that the optical path length difference is equal to or larger than 22/n mm in air in a case where the generated clock has a frequency n times a frequency of the interferometer corresponding to the optical path length difference, n being an integer equal to or larger than 1.

Further features of the present invention will become apparent from the following description of exemplary embodiments with reference to the attached drawings.

BRIEF DESCRIPTION OF DRAWINGS

FIG. 1 is a schematic diagram illustrating an example of an OCT apparatus according to the present embodiment.

FIG. 2A is a schematic diagram illustrating a method of scanning illumination light performed by a scan unit of the OCT apparatus according to the present embodiment.

FIG. 2B is a schematic diagram illustrating a method of scanning illumination light performed by the scan unit of the OCT apparatus according to the present embodiment.

FIG. 2C is a schematic diagram illustrating a method of scanning illumination light performed by the scan unit of the OCT apparatus according to the present embodiment.

FIG. 2D is a schematic diagram illustrating a method of scanning illumination light performed by the scan unit of the OCT apparatus according to the present embodiment.

FIG. 3 is a schematic diagram of an eyeball relating to the present embodiment.

FIG. 4 is a diagram for describing an issue concerning a wider angle of view relating to the present embodiment.

FIG. 5A is a diagram for describing changes in the optical frequency of a tunable light source according to the present embodiment.

FIG. 5B is a diagram for describing a k-clock according to the present embodiment.

FIG. 6 is a schematic diagram of a k-clock generator according to the present embodiment.

FIG. 7A is a diagram for describing the sampling theorem relating to the present embodiment.

FIG. 7B is a diagram for describing the sampling theorem relating to the present embodiment.

FIG. 8 is a schematic diagram of a k-clock generator configured by using a double-path interferometer.

FIG. 9 is a table illustrating relationships among the depth ranges of a tomographic image (within the eyeball and in air), the number of samples N, the clock frequency fs, and the optical path length difference of a k-clock interferometer.

DESCRIPTION OF EMBODIMENTS

With a method according to the related art, image processing for combining together a plurality of successive tomographic images that have been obtained takes longer and is troublesome. Accordingly, it is desirable that a tomographic image of a wide area is obtained by performing a single image capture operation. In this case, however, because the eyeball is substantially spherical, the optical path length of illumination light in a central portion of the fundus is significantly different from that in a peripheral portion thereof. Consequently, with the configuration of an OCT apparatus according to the related art, it is difficult to comprehensively capture a tomographic image of the fundus in a desired depth range with a single scan operation over a wide area of the fundus.

In an SS-OCT apparatus, a clock generator is typically used. The clock generator is configured as an interferometer including an optical path through which part of light emitted from a swept light source passes, the optical path being split into a first optical path and a second optical path having an optical path length difference relative to the first optical path, to generate a clock used by an A/D converter sampling an analog signal.

In view of the issue described above, the present embodiment provides a clock generator that is configured so that a tomographic image of the fundus in a desired depth range can be comprehensively obtained with a single scan operation over a wide area of the fundus.

An imaging apparatus according to the present embodiment is an SS-OCT apparatus and includes an interference unit (for example, an OCT interference unit 20 described below) and a detector (for example, a photodetector) that detects interference light generated as a result of interference at the interference unit. The imaging apparatus according to the present embodiment further includes a converter (for example, an A/D converter 32 described below) that converts an analog signal (an electrical signal) generated from the interference light detected by the detector into a digital signal. The imaging apparatus according to the present embodiment further includes a clock generator that is configured as an interferometer including an optical path through which part of light emitted from a swept light source passes, the optical path being split into a first optical path and a second optical path having an optical path length difference relative to the first optical path, to generate a clock used by the converter sampling the analog signal. Here, the light source according to the present embodiment is a light source for an SS-OCT apparatus which sweeps the wavelength of the emitted light, and is also called a swept light source. The clock generator according to the present embodiment is a k-clock generator 80 described below, for example. The imaging apparatus according to the present embodiment further includes a tomographic image obtaining unit that obtains a tomographic image of the fundus by using the digital signal converted from the analog signal sampled by the converter in accordance with the generated clock.

A scan unit according to the present embodiment is configured to scan the illumination light across the fundus over a scan angle equal to or larger than 47 degrees in terms of the angle in air. Accordingly, the image capture range (scanning range) in the planar direction of the fundus can be 14 mm or more. The clock generator according to the present embodiment is configured so that the optical path length difference of the interferometer is 22/n mm or more in air in a case where the clock frequency is n times (n is an integer equal to or larger than 1) the frequency of the interferometer, the frequency of the interferometer corresponding to the optical path length difference of the interferometer. In this case, the depth range of a tomographic image can be one-fourth the optical path length difference, namely, 5.5 mm or more, which is equal to 4.0 mm or more within the eyeball. Accordingly, by configuring the optical path length difference of the clock generator as described above, it is possible to comprehensively obtain a tomographic image of the fundus in a desired depth range with a single scan operation over a wide area of the fundus.

The optical path length difference of the interferometer of the clock generator corresponds to the clock used by the converter sampling an analog signal, and therefore, the sampling theorem needs to be considered when the optical path length difference is determined. According to the sampling theorem, it is not possible to obtain a tomographic image with high accuracy in a range equal to or larger than half the optical path length difference. In a general clock generator, a single-path interferometer is used, and therefore, it is assumed that a single-path interferometer is used as the interferometer of the clock generator. The sample optical path of an OCT apparatus is configured as a double path, and therefore, the depth range of a tomographic image is half the optical path length difference of the interferometer of the clock generator. Consequently, the depth range of a tomographic image is equal to one-quarter of the optical path length difference of the interferometer of the clock generator as a result of calculation. The relationship between the optical path length difference and the depth range is described in detail below.

It is ideal that a swept light source, which is the light source in the present embodiment, is configured to emit light of each wavelength while the light lineally changes over time. However, in a general swept light source, in actuality, the light does not lineally change with accuracy but non-lineally changes, and a mode hop (an event in which the wavelength changes non-continuously at a certain timing) or the like may occur. That is, with a swept light source, it is difficult to accurately sweep the wavelength in accordance with a setting. Therefore, the clock generator described above is used to adjust the timing at which the converter converts an analog signal into a digital signal. Here, it is desirable that the clock generator generates a clock so that the converter samples an analog signal at substantially equal wavenumber intervals. By doing so, it is possible to easily perform conversion from the wavenumber space into the real space without performing interpolation or the like. However, the present invention is not limited to the above. Sampling at substantially equal wavenumber intervals need not be performed. If such sampling is not performed, interpolation or the like is performed to thereby perform conversion from the wavenumber space into the real space.

A light source 10 in the present embodiment is not limited to a specific light source as long as the light source 10 is a light source that changes the wavelength of the light. In order to obtain information about an object by using an OCT apparatus, the wavelength of the light emitted from the light source needs to be continuously changed. As the light source 10 in the present embodiment, an external-resonator-type swept light source that uses a diffraction grating, a prism, and so on, or an external-resonator-type light source of any type using a resonator-length-variable Fabry-Perot tunable filter may be used, for example. Alternatively, a superstructure-grating distributed Bragg reflector (SSG-DBR) that changes the wavelength by using a sampled grating, a tunable vertical-cavity surface-emitting laser (VCSEL) using the micro-electro-mechanical systems (MEMS) mechanism (MEMS-VCSEL), or the like may be used. Also, a fiber laser may be used. The fiber laser may be based on a dispersion tuning scheme or a Fourier domain mode locking scheme. Examples of an external-resonator-type swept light source using a diffraction grating, a prism, and so on include a swept light source in which a resonator is equipped with a diffraction grating, the light is separated by the diffraction grating, and the wavelength of the emitted light is continuously changed by using a polygon mirror or a stripe-shaped reflection mirror provided on a rotating disk. In general, a VCSEL is configured as a surface-emitting laser that includes a lower reflection mirror, an active layer, and an upper reflection mirror in this order, has a cavity between the active layer and the upper reflection mirror, and changes the position of at least one of the upper reflection mirror and the lower reflection mirror in the optical axis direction to change the wavelength of the emitted light.

Hereinafter, an embodiment of the present invention will be described with reference to the drawings. An embodiment described below is not intended to limit the present invention described in the appended claims, and all of the combinations of features described in the present embodiment are not necessarily essential to a solution provided by the present invention. For example, an OCT apparatus according to the present embodiment is configured by using a Mach-Zehnder interferometer; however, the present invention is not limited to this. The OCT apparatus may be configured by using a Michelson interferometer. The OCT apparatus according to the present embodiment is configured to change the reference optical path length; however, the present invention is not limited to this. The OCT apparatus may be configured to change the optical path length difference between the reference light and the measurement light. For example, the reference optical path length may be fixed while the measurement optical path length may be changed.

Configuration of SS-OCT

FIG. 1 is a diagram illustrating an example configuration of an imaging apparatus based on an optical coherence tomography imaging method (OCT apparatus) according to an embodiment of the present invention. The OCT apparatus includes the light source 10 that sweeps the optical frequency of the emitted light, the OCT interference unit 20 that generates interference light, a detector 30 that detects the interference light, and an information obtaining unit 40 that obtains information about the fundus of an object 100. The information obtaining unit 40 also functions as a tomographic image obtaining unit (image generation unit) that obtains (generates) a tomographic image of the fundus. The OCT apparatus further includes a measurement arm 50 and a reference arm 60.

The OCT interference unit 20 includes couplers 21 and 22. The coupler 21 splits light emitted from the light source 10 into illumination light that is incident on the fundus and reference light. The illumination light passes through the measurement arm 50 and is incident on the object 100. More specifically, the illumination light that enters the measurement arm 50 passes through a polarization controller 51 at which the polarization state thereof is adjusted, and is thereafter emitted from a collimator 52 as spatial light. Thereafter, the illumination light passes through an X-axis scanner 53, a Y-axis scanner 54, and a focus lens 55 and is incident on the fundus of the object 100. The X-axis scanner 53 and the Y-axis scanner 54 constitute the scan unit having a function of scanning the fundus with the illumination light.

With the scan unit, a position on the fundus which is illuminated with the illumination light can be changed. The back-scattered light (reflection light) from the fundus passes through the focus lens 55, the Y-axis scanner 54, the X-axis scanner 53, the collimator 52, and the polarization controller 51, is emitted from the measurement arm 50, and enters the coupler 22 via the coupler 21.

On the other hand, the reference light passes through the reference arm 60 and enters the coupler 22. More specifically, the reference light that enters the reference arm 60 passes through a polarization controller 61 at which the polarization state thereof is adjusted, and is thereafter emitted from a collimator 62 as spatial light. Thereafter, the reference light passes through a dispersion compensation glass component 63, an optical-path-length adjusting optical system 64, and a dispersion adjusting prism pair 65, enters an optical fiber via a collimator lens 66, is emitted from the reference arm 60, and enters the coupler 22.

The reflection light from the object 100 which passes through the measurement arm 50 and the reference light which passes through the reference arm 60 interfere with each other at the coupler 22 to generate interference light. Then, the interference light is detected by the detector 30. The detector 30 includes a differential detector 31 and the A/D converter 32. In the detector 30, the differential detector 31 detects interference light beams separated immediately after the interference light has been generated at the coupler 22. Then, the differential detector 31 converts the OCT interference signal into an electrical signal, and the A/D converter 32 converts the electrical signal into a digital signal. The digital signal is sent to the information obtaining unit 40 at which a frequency analysis, such as Fourier transform, is performed on the digital signal to thereby obtain information about the fundus. The obtained information about the fundus is displayed on a display 70 as a tomographic image.

The imaging apparatus according to the present embodiment may further include an analysis unit that analyzes the obtained tomographic image to perform segmentation into a plurality of layers, and the information obtaining unit 40 may function as the analysis unit, for example. In this case, the imaging apparatus may further include an image generation unit that generates a planar image along any of the plurality of layers in accordance with an analysis result from the analysis unit, and the information obtaining unit 40 may function as the image generation unit, for example. The imaging apparatus may further include a display controller that displays the planar image and the tomographic image on the display 70 while the positions of the macula and the optic disc of the fundus which are included in the planar image are associated with the positions of the macula and the optic disc of the fundus which are included in the tomographic image, and the information obtaining unit 40 may function as the display controller, for example. As a result, it is possible to observe the planar image along any of the plurality of layers over a wider angle of view, resulting in increased diagnostic efficiency and diagnostic accuracy. The imaging apparatus may further include a computation unit that generates curvature information about the fundus including the macula and the optic disc of the fundus by using a tomographic image of the macula and the optic disc of the fundus, and the information obtaining unit 40 may function as the computation unit, for example. As a result, it is possible to quantitatively evaluate the curvature of the fundus over a wider angle of view, resulting in increased diagnostic efficiency and diagnostic accuracy. In order to obtain a tomographic image of the fundus including the macula and the optic disc, the scan unit may be controlled so that the macula and the optic disc are illuminated with the illumination light with a single scan operation. Alternatively, a 3D tomographic image of the fundus is obtained, and thereafter, a tomographic image including the macula and the optic disc may be recreated from the 3D tomographic image.

In the OCT apparatus illustrated in FIG. 1, sampling of interference light is performed at equal optical frequency (equal wavenumber) intervals on the basis of a k-clock signal issued from the k-clock generator 80 provided outside the light source 10. In order to split the light emitted from the light source 10 and to direct part of the light into the k-clock generator 80, a coupler 90 is provided. The k-clock generator 80 and the coupler 90 may be built into the light source 10.

The process described above is a process for obtaining information about a cross section at a certain point of the object 100, and such a process for obtaining information about a cross section in the depth direction of the object 100 is called an A-scan. A scan for obtaining information about a cross section of an object in a direction orthogonal to the direction of an A-scan, that is, a scan for obtaining a 2D image, is called a B-scan. A scan performed in a direction orthogonal to both the direction of an A-scan and the direction of a B-scan is called a C-scan. In a case of performing a 2D raster scan on the fundus plane for obtaining a 3D tomographic image, a high-speed scanning direction corresponds to a B-scan, and a low-speed scanning direction that is orthogonal to the direction of the B-scan corresponds to a C-scan. A 2D tomographic image is obtained by performing an A-scan and a B-scan, and a 3D tomographic image is obtained by performing an A-scan, a B-scan, and a C-scan. A B-scan and a C-scan are performed by using the X-axis scanner 53 and the Y-axis scanner 54 described above.

Note that the X-axis scanner 53 and the Y-axis scanner 54 are constituted by polarization mirrors that are arranged so that their rotation axes are orthogonal to each other. The X-axis scanner 53 is responsible for a scan in an X-axis direction, and the Y-axis scanner 54 is responsible for a scan in a Y-axis direction. The X-axis direction and the Y-axis direction are directions perpendicular to the eye axis direction of the eyeball and are orthogonal to each other. The line scanning directions of a B-scan and a C-scan need not match the X-axis direction and the Y-axis direction. Therefore, the line scanning directions of a B-scan and a C-scan can be determined as appropriate in accordance with a 2D tomographic image or a 3D tomographic image that is to be captured.

By driving both the X-axis scanner 53 and the Y-axis scanner 54 and changing the angles of the polarization mirrors, various scans can be performed. For example, raster scans as illustrated in FIGS. 2A and 2B may be performed, or a scan as illustrated in FIG. 2C may be performed in which the scan line passes through one point (the macula, for example) of the eyeball a plurality of times. A spiral scan centered around one point (the macula, for example) of the eyeball as illustrated in FIG. 2D may be performed.

Scan Angle

Regarding fundus examinations, it is desirable to capture an image of the macula and the optic disc with a single scan operation. A range (scan angle) over which the illumination light of the OCT apparatus is scanned and which is required in order to meet the desire is described with reference to FIG. 3. FIG. 3 is a schematic diagram of an eyeball while the eyeball is assumed to be spherical. The macula is located on the side opposite to the pupil center of the eyeball. The optic disc is located a short distance away from the macula. The macula and the optic disc are especially important regions in the fundus.

Regarding the fundus of a normal adult, the distance D between and inclusive of the macula and the optic disc is about 5.75 mm. The illumination light is emitted so as to enter the pupil center of the eyeball and to circle around and scan the fundus. In a case of capturing an image of an area centered around the macula and including the optic disc with a single scan operation, the length L of a shortest curve that connects the macula and the optic disc, namely, the image capture range, needs to be about 14 mm by taking into consideration variations among individuals. Here, the deflection angle of measurement light that is emitted so as to enter the pupil center and circle around the fundus is denoted by α, the deflection angle corresponding to the image capture range. The diameter of the eyeball of an adult is about 24 mm on average. Therefore, in order to set the image capture range L to 14 mm or more, the deflection angle α needs to be 33.4 degrees or more. When this angle is represented as the deflection angle β of the illumination light in air which is incident on the pupil center while the average refractive index within the eyeball is assumed to be 1.38, the deflection angle β is about 47 degrees (arcsin(1.38× sin(33.4 degrees/2))×2 nearly equals 47 degrees). That is, in order to capture an image of the macula and the optic disc at once while the image is centered around the macula, in a case of lineally scanning the fundus with illumination light, it is sufficient that the angle range for scanning the fundus is 47 degrees or more in terms of the angle in air. Hereinafter, the angle range for scanning the fundus in the case of linearly scanning the fundus with illumination light in terms of the angle in air is assumed to be the angle of view. That is, the deflection angle β is defined as the angle of view.

Now, a problem that may arise when a scan is performed over the above-described deflection angle β is described with reference to FIG. 4. FIG. 4 is a schematic diagram of an eyeball while the eyeball is assumed to be spherical as in FIG. 3. The dashed line in FIG. 4 represents a scanning trajectory. As illustrated in FIG. 4, the physical distance from the pupil center to the outer layer of the eyeball, namely, the fundus, is equal to a +b at the macula and is equal to a at a position located away from the macula (that is, a position corresponding to the angle θ/2). The distances a and b are expressed by the following expressions by using the length T that is the eye axis length and the deflection angle θ within the eyeball:

$$a = T \times \cos(\theta/2) \qquad \text{expression 1,}$$

$$a + b = T \qquad \text{expression 2.}$$

As described above, the distance from the pupil center to the macula is different from the distance from the pupil center to the position away from the macula by b. The value of b increases as the angle θ becomes larger. As a result, with an OCT apparatus for fundus examinations having a wider angle of view, the optical path length from the pupil center to the macula is significantly different from the optical path length from the pupil center to a peripheral position that is away from the macula. The eye axis lengths T of adults significantly vary among individuals, and the range of the eye axis length T into which the eye axis lengths of 95% of adults fall is between and inclusive of 21 mm and 28 mm. Here, if the maximum value of the range, namely, 28 mm, is used as the value of the eye axis length T, and the deflection angle θ within the eyeball is assumed to be 33.4 degrees, the value of b is about 1.2 mm from expressions 1 and 2.

Fundus tissues observed by using an OCT apparatus for fundus examinations are the retina in the proximity of the surface of the fundus and the choroid lying behind the retina. The retina has a maximum thickness of about 0.50 mm, and the choroid has a maximum thickness of about 0.30 mm. Therefore, an OCT apparatus for fundus examinations needs to be capable of capturing images of a portion at the depth of at least 0.80 mm. That is, the surface of the fundus and the choroid has a distance difference of 0.8 mm therebetween.

Therefore, in order to capture an image of the macula and the optic disc with a single scan operation and to obtain information about the vicinity of the surface of the optic disc and about the choroid lying behind the macula, a distance difference of about 4.0 mm (2×(b+0.80) nearly equals 4.0) is required. This distance difference corresponds to about 5.5 mm (4.0 mm×1.38 nearly equals 5.5 mm) in terms of the optical path length difference in air. That is, even if the angle of view is assumed to be 47 degrees or more, in order to implement an OCT apparatus with which tomographic information can be obtained, an optical path length difference of 5.5 mm in air is required.

In an OCT apparatus based on a Fourier domain scheme, such as an SS-OCT apparatus, a Fourier transform process is performed on obtained interference signal data in the wavenumber space, and distance information is output. In a case of an SS-OCT apparatus, data is obtained in the time domain by using an A/D converter. Here, if the optical frequency of light emitted from a tunable light source linearly changes relative to time with accuracy, data at equal frequency intervals, that is, data at equal wavenumber intervals, can be obtained by performing sampling at equal time intervals. However, as schematically illustrated in FIG. 5A, wavelength sweeping is performed on the optical frequency of the tunable light source by changing the resonator length using a driving mechanism generally, and therefore, the optical frequency of the tunable light source is non-linear relative to time. As a result, even if a Fourier transform process is performed on the basis of sampling at equal time intervals, obtained data is not data at equal wavenumber intervals, and distance information is not obtained. Accordingly, in an SS-OCT apparatus, data is generally obtained by using a k-clock, which is a sampling clock generated at equal wavenumber intervals.

Clock Generator

Now, the k-clock generator 80 is described with reference to FIG. 6. The reference numerals in FIG. 6 correspond to those in FIG. 1. Light emitted from the light source 10 is split at the coupler 90 having a split ratio of 95 to 5, for example, and part of the light enters the k-clock generator 80 as split light. The split light is further split at a coupler 81 and is directed to two optical paths, which are formed as a first optical path and a second optical path. The first optical path and the second optical path are provided so as to have an optical path length difference 82 therebetween, and the light beams passing through the two optical paths interfere with each other at a coupler 83. In doing so, a k-clock interferometer is configured. The k-clock generator 80 further includes a correction circuit 84 that receives the resulting interference signal from the k-clock interferometer, converts the received interference signal into an electrical signal, and performs amplitude correction. The optical path length difference 82 for a k-clock corresponds to a clock frequency fs described below.

In the second optical path having the optical path length difference relative to the first optical path, a substance (a gas or the like) with which the refractive index can be changed may be provided, for example. In a case where a configuration is employed in which light is emitted from a fiber to air and thereafter enters another fiber, the optical distance between the fibers may be changed to thereby provide the optical path length difference. In the above-described configuration in which light is once emitted outside a fiber, the optical path length difference may be changed by using a plurality of folding mirrors provided on a movable stage and moving the folding mirrors in the optical axis direction. A mechanism for implementing the techniques described above is called a change unit. Here, a controller controlling the change unit, which changes the optical path length difference in accordance with the scan angle, may be provided. For example, when the scan angle is made larger, unnecessary image capture operations in the depth range can be reduced by making the optical path length difference larger, resulting in a reduced image capture time. Here, the scan unit may be configured so that the scan angle is changeable within a range between a first angle, which is equal to or larger than 47 degrees, and a second angle, which is smaller than 47 degrees. The clock generator may be configured so that the optical path length difference is changeable within a range between a first optical path length difference, which is equal to or larger than 22 mm, and a second optical path length difference, which is smaller than 22 mm.

The imaging apparatus according to the present embodiment may further include a selection unit that selects an image capture mode from among a plurality of image capture modes corresponding to different scan angles. Here, the controller may control the scan unit and the change unit so as to change the scan angle and the optical path length difference in accordance with the selected image capture mode. For example, the scan angle used in an image capture mode in which an image that includes both the macula and the optic disc is captured as a tomographic image is larger than that used in an image capture mode in which an image that includes one of the macula and the optic disc is captured as a tomographic image, and therefore, the optical path length difference for the former image capture mode may be made larger. The selection unit may be configured to be able to select the distance of a tomographic image in the depth range. Here, the selection unit may be configured to be able to select the distance within a range between a first distance, which is equal to or larger than 4.0 mm within the eyeball, and a second distance, which is smaller than 4.0 mm within the eyeball. Here, if the distance becomes smaller, the optical path length difference may be changed so as to become smaller. The selection unit may be configured to be able to select an image capture mode from among a plurality of image capture modes including an image capture mode in which an image is captured so as to include the vitreous body, the retina, and the choroid of the eye. If the image capture mode in which an image is captured so as to include the vitreous body, the retina, and the choroid of the eye is selected, a tomographic image of the fundus at a distance equal to or larger than 4.0 mm within the eyeball in the depth range may be obtained. This is because, in order to capture a tomographic image so as to include the vitreous body, the retina, and the choroid of the eye without omission, the distance of 4.0 mm or more within the eyeball in the depth range is required. Even if the clock generator is configured so that the number of times sampling is performed or the clock frequency is changed with simulation as described below instead of the optical path length difference being changed, similar effects can be attained. For example, the clock generator may be configured so that the number of times sampling is performed or the clock frequency is decreased when the distance of a tomographic image in the depth range becomes smaller.

Optical Path Length Difference of Interferometer of Clock Generator

A k-clock interference signal takes the form of a sign wave as the optical frequency changes over time. The optical frequency non-lineally changes over time, and therefore, the cycle of the sign wave changes over time. However, the sign wave appears at equal intervals in terms of the frequency domain. That is, the zero-crossing point or the peak point of the k-clock interference signal appears at equal wavenumber intervals. Therefore, if sampling is performed by using the zero-crossing point or the peak point as a clock position as illustrated in FIG. 5B, an OCT interference signal in the wavenumber space can be obtained. The amplitude of the obtained k-clock interference signal is corrected by using an amplifier or the like so as to obtain an amplitude and a voltage adaptable to an A/D converter, thereby generating a k-clock. A k-clock is a sampling clock, and therefore, a k-clock needs to be based on the sampling theorem. For example, in a case where the frequency of the OCT interference signal is equal to or smaller than half the clock frequency fs as illustrated in FIG. 7A, the original signal can be reproduced. In a case where the frequency of the OCT interference signal is equal to or larger than half the clock frequency fs as illustrated in FIG. 7B, a false signal is obtained. Therefore, the sampling theorem specifies that the clock frequency fs needs to be equal to or larger than twice the frequency of the OCT interference signal.

An interference phenomenon occurs when the optical path length difference between two optical paths is equal to n times the wavelength $\lambda$, namely equal to $n\lambda$, where n is an integer. Therefore, the spacing between interference fringes becomes narrow in proportion to the optical path length difference, and the frequency of the signal increases. That is, in order to set the clock frequency fs to a value equal to or larger than twice the frequency of the OCT interference signal, the optical path length difference 82 needs to be set to a value equal to or larger than twice the upper limit of the distance in the depth direction. Specifically, by taking into consideration the sampling theorem, the optical path length difference 82 for a k-clock needs to be set to a value equal to or larger than twice the depth range of a required tomographic image. As described above, in the case where the depth range of a tomographic image is to be set to 5.5 mm or more in air (4.0 mm or more within the eyeball), the optical path length difference 82 for a k-clock needs to be set to 11 mm or more in air.

The sample optical path of an OCT interferometer is usually configured as a double path that is constituted by an optical path through which illumination light is incident on the fundus and an optical path through which reflection light returns from the fundus. On the other hand, the optical path of a general k-clock interferometer is configured as a single path in which light is split, the split light beams pass through optical paths having an optical path length difference therebetween, and thereafter the split light beams are combined without being reflected. Therefore, in a case where the k-clock interferometer is configured by using a single path, the optical path length difference 82 for a k-clock needs to be further increased to a value twice the above-described value of 11 mm or more, namely, 22 mm or more in air. That is, in the case where the k-clock interferometer is configured by using a single path, the optical path length difference 82 for a k-clock needs to be set to a value equal to or larger than four times the depth range of a required tomographic image. In doing so, the depth range of a tomographic image can be set to 4.0 mm or more within the eyeball. The k-clock interferometer can be configured as a double-path interferometer as illustrated in FIG. 8. Reference numerals in FIG. 8 correspond to those in FIG. 1 and FIG. 6. As described above, in a case where the k-clock interferometer is configured by using a double path, the optical path length difference 82 for a k-clock needs to be set to a value equal to or larger than twice the depth range of a required tomographic image by taking into consideration the sampling theorem.

Regarding the optical path length difference of the k-clock interferometer, generally, measurement of a portion from the choroid to the boundary of the sclera is performed over a scan angle for scanning the fundus of about 40 degrees in terms of the angle in air, and therefore, the depth range (the distance in the depth direction of a tomographic image) of about 2.6 mm within the eyeball is required, which corresponds to the depth range of about 3.6 mm in terms of the length in air. Accordingly, the optical path length difference of a single-path k-clock interferometer is 14.4 mm (3.6 mm×4=14.4 mm) in terms of the length in air, and therefore, is set to about 15 mm when designed. However, in the case where the optical path length difference of a k-clock interferometer is about 15 mm in terms of the length in air, a wider angle of view may cause a problem, that is, the image may be folded in the peripheral portion of the fundus. That is, in order to obtain tomographic information over an angle of view of 47 degrees or more while the depth range is set to 5.5 mm or more in air, the optical path length difference of the k-clock interferometer needs to be set to 22 mm or more. In the example in FIG. 6, the k-clock generator 80 is provided outside the light source 10; however, the k-clock generator 80 may be included in the light source 10. By including the k-clock generator 80 in the light source 10, the configuration of the imaging apparatus can be simplified. In order to attain the optical path length difference for a k-clock of 22 mm, the coherent length is preferably 14 mm or more. As described above, by setting the optical path length difference of the interferometer in the clock generator to 22 mm or more, it is possible to comprehensively obtain a tomographic image of the fundus in a desired depth range with a single scan operation over a wide area of the fundus.

Here, if the depth range (measurement distance) of a tomographic image is denoted by $\Delta z$, the center wavelength is denoted by $\lambda c$, and the swept wavelength width is denoted by $\Delta \lambda$, then, the number of samples N, which is the number of times sampling is performed in a single sampling operation over the entire depth range of the tomographic image, is calculated by using an expression, $(4 \times \Delta z \times \Delta \lambda)/\lambda c^2$. If the wavelength sweeping frequency is denoted by fA, and the duty ratio (a period in which effective light emission is performed as OCT during a single sweeping operation) is denoted by d, then, the clock frequency fs is calculated by using an expression, $(N \times fA)/d$. In the light source according to the present embodiment, it is assumed that $\lambda c$ is equal to 1040 nm, $\Delta \lambda$ is equal to 110 nm, fA is equal to 100 kHz, and d is equal to 0.446. Then, in a case where the depth range of a tomographic image is 5.5 mm in air (4.0 mm within the eyeball) according to the present embodiment, the number of samples N is equal to 2237 (($4 \times 5.5 \times 10^6 \times 110)/1040^2 = 2237$). In this case, the clock frequency fs is equal to 501.57 MHz (($2237 \times 100 \times 10^3)/0.446 = 501.57$). In a case where the depth range of a tomographic image is 3.6 mm in air (2.6 mm within the eyeball) according to the related art, the number of samples N is equal to 1464 (($4 \times 3.6 \times 10^6 \times 110)/1040^2 = 1464$). In this case, the clock frequency fs is equal to 328.25 MHz (($1464 \times 100 \times 10^3)/0.446 = 328.25$). Consequently, in order to comprehensively obtain a tomographic image of the fundus in a desired depth range with a single scan operation over a wide area of the fundus, the clock generator may be configured so that the number of times sampling is performed in a single sampling operation over the entire depth range of the tomographic image is about 2200 times or more. Further, in order to comprehensively obtain a tomographic image of the fundus in a desired depth range with a single scan operation over a wide area of the fundus, the clock generator may be configured so that the clock frequency is about 500 MHz or more.

In the above description, it is assumed that the k-clock interferometer frequency fk, which corresponds to the optical path length difference of the k-clock interferometer, is equal to the clock frequency fs. Now, a case is considered where the clock frequency fs is n times (n is an integer equal to or larger than 1) the k-clock interferometer frequency fk, that is, the k-clock interferometer frequency fk multiplied by n equals the clock frequency fs (fk×n=fs). Note that, in a case where n is an integer equal to or larger than 2, fs=fk×n is satisfied by using a method of electrically increasing the frequency. In the case where the depth range of a tomographic image is 5.5 mm or more in air (4.0 mm or more within the eyeball), the clock generator is configured so that the optical path length difference of the k-clock interferometer is 22/n mm or more in air. Here, the clock generator may be configured by using a single path. In a case where the clock generator is configured by using a double path, the clock generator is configured so that the optical path length difference of the k-clock interferometer is 11/n mm or more. Here, the number of samples N is equal to 2237 and the clock frequency fs is equal to 501.57 MHz as calculated above regardless of the value of n.

In a case where the depth range of a tomographic image is 6.9 mm or more in air (5.0 mm or more within the eyeball), the optical path length difference of the k-clock interferometer is preferably 27.6/n mm or more in air in the case where the clock generator is configured by using a single path. In the case where the clock generator is configured by using a double path, the optical path length difference of the k-clock interferometer is preferably 13.8/n mm or more. Here, the number of samples N is equal to 2807 (($4 \times 6.9 \times 10^6 \times 110)/1040^2 = 2807$). Therefore, the clock generator may be configured so that the number of times sampling is performed in a single sampling operation over the depth range of the tomographic image is 2800 or more. The clock frequency fs is equal to 629.37 MHz (($2807 \times 100 \times 10^3)/0.446 = 629.37$). Therefore, the clock generator may be configured so that the clock frequency fs is 620 MHz or more.

In a case where the depth range of a tomographic image is 8.0 mm or more in air (5.8 mm or more within the eyeball), the optical path length difference of the k-clock interferometer is preferably 32/n mm or more in air in the case where the clock generator is configured by using a single path. In the case where the clock generator is configured by using a double path, the optical path length difference of the k-clock interferometer is preferably 16/n mm or more. Here, the number of samples N is equal to 3254 (($4 \times 8.0 \times 10^6 \times 110)/1040^2 = 3254$). Therefore, the clock generator may be configured so that the number of times sampling is performed in a single sampling operation over the depth range of the tomographic image is 3200 or more. The clock frequency fs is equal to 729.60 MHz (($3254 \times 100 \times 10^3)/0.446 = 729.60$). Therefore, the clock generator may be configured so that the clock frequency fs is 720 MHz or more. The relationships among the depth ranges of a tomographic image (within the eyeball and in air), the number of samples N, the clock frequency fs, and the optical path length difference of the k-clock interferometer are shown by a table in FIG. 9.

The clock generator may be configured so that the frequency of the interferometer is converted into an integer multiple of the frequency of the interferometer, the integer multiple being equal to or larger than 2, the converted frequency being used as the clock frequency. As described below, a method of electrically increasing the frequency is available. For example, as described in NPL 1, the frequency can be increased by using a method of providing a frequency doubler in a stage before a signal is input to a data acquisition (DAQ) card. By using two DAQ cards, in a front stage of a functional block that functions as a converter for sampling an analog signal generated from detected OCT interference light, the frequency of the k-clock interferometer can be converted into a frequency twice thereof.

The tomographic image obtaining unit may be configured to obtain tomographic data of the fundus at the distance equal to or larger than 4.0 mm within the eyeball in the depth range and to generate a new tomographic image by removing, from the obtained tomographic image, part of the obtained tomographic image corresponding to part of the depth range. For example, the tomographic image obtaining unit obtains tomographic data for a depth range of 8.0 mm in air (5.8 mm within the eyeball) and generates, from the obtained data, a tomographic image that corresponds to a depth range of 6.9 mm in air (5.0 mm within the eyeball) by removing an upper portion and a lower portion in the depth range, which include noise. More specifically, the tomographic image obtaining unit first generates 4096 pieces of data in a single A-scan by performing fast Fourier transform (FFT) on the OCT interference signal. The number of pieces of data is 4096 because the n-th power of 2 that is close to 3254, which is the number of samples N described above, is the twelfth power of 2. The 4096 pieces of data include a real image and a virtual image with the coherence gate as a boundary therebetween. Therefore, half of the pieces of data, namely, 2048 pieces of data are pieces of data in the vertical direction. The number of pieces of data in the horizontal direction is 1024, which is the number of A-scan lines. Here, it is assumed that the center wavelength λc is equal to 1040 nm and the swept wavelength width Δλ is equal to 110 nm as described above. Then, the vertical resolution, which is the optical resolution in the depth direction, is about 8 μm. In order to reproduce the vertical resolution of 8 μm, a pixel resolution that is equal to or smaller than half the vertical resolution is required. Here, a case of assigning 4 μm per pixel is considered. In this case, the depth range is 5.8 mm within the eyeball, and therefore, the number of pixels in the vertical direction is equal to 1450 (5800÷4=1450). In a case of generating a tomographic image that corresponds to the depth range of 5.0 mm within the eyeball, 200 pixels are removed (1450−5000÷4=200), for example. An area on the lower frequency side is an area that indicates a DC component present in the vicinity of the coherence gate of the tomographic image, and therefore, 15 pixels in an upper portion of the tomographic image are removed, for example. Regarding the remaining 185 pixels (200−15=185), the 185 pixels, which are present in a lower portion of the tomographic image, are removed. By using 1250 pixels obtained by removing the 200 pixels as described above, the tomographic image that corresponds to the depth range of 5.0 mm within the eyeball can be generated. A noise component, such as a DC component, has been removed from the generated tomographic image, and therefore, the image quality of the generated tomographic image is better than the tomographic image that corresponds to the depth range of 5.0 mm within the eyeball obtained with the number of samples N equal to 2807 described above.

Note that the present invention is not limited to a single scan operation over a wide area of the fundus. That is, the present invention is not limited to the case where the scan unit is configured to scan the illumination light across the fundus over the scan angle that is equal to or larger than 47 degrees in terms of the angle in air. Regardless of the scan angle, in a case where a tomographic image of the fundus at the distance equal to or larger than 4.0 mm within the eyeball in the depth range is to be obtained, the clock generator needs to be configured so that the optical path length difference corresponds to the distance of 4.0 mm or more within the eyeball. Here, if the second optical path is configured by using a single path, the clock generator may be configured so that the optical path length difference is 22 mm or more in air. If the second optical path is configured by using a double path, the clock generator may be configured so that the optical path length difference is 11 mm or more in air. Even if the clock generator is configured so that the number of times sampling is performed or the clock frequency is changed with simulation instead of the optical path length being set to the length described above, similar effects can be attained.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-094340, filed May 1, 2015 and Japanese Patent Application No. 2015-175019, filed Sep. 4, 2015, which are hereby incorporated by reference herein in their entirety.

The invention claimed is:

1. An imaging apparatus comprising:
a light source configured to emit light while sweeping a wavelength of the light;
an interference unit configured to split the light emitted from the light source into illumination light that is incident on a fundus and reference light and to generate interference light obtained by reflection light reflected from the fundus on which the illumination light is incident interfering with the reference light;
a scan unit configured to scan the illumination light across the fundus;
a detector configured to detect the interference light generated by the interference unit;
a converter configured to convert an analog signal generated from the interference light detected by the detector into a digital signal;
a clock generator configured as an interferometer including an optical path through which part of the light emitted from the light source passes, the optical path being split into a first optical path and a second optical path having an optical path length difference relative to the first optical path, to generate a clock used by the converter sampling the analog signal; and
a processor including a tomographic image obtaining unit configured to obtain a tomographic image of the fundus by using the digital signal converted from the analog signal sampled by the converter in accordance with the generated clock, wherein
the scan unit is configured to scan the illumination light across the fundus over a scan angle equal to or larger than 47 degrees in air,
the tomographic image obtaining unit is configured to obtain a tomographic image of the fundus at a distance equal to or larger than 4.0 mm within an eyeball in a depth range, and
the clock generator is configured so that the optical path length difference is equal to or larger than 22/n mm in air in a case where the generated clock has a frequency n times a frequency of the interferometer corresponding to the optical path length difference, n being an integer equal to or larger than 1.

2. The imaging apparatus according to claim 1, wherein
the tomographic image obtaining unit is configured to obtain a tomographic image of the fundus at a distance equal to or larger than 5.0 mm within the eyeball in the depth range, and
the clock generator is configured so that the optical path length difference is equal to or larger than 27.6/n mm in air.

3. The imaging apparatus according to claim 1, wherein
the tomographic image obtaining unit is configured to obtain a tomographic image of the fundus at a distance equal to or larger than 5.8 mm within the eyeball in the depth range, and
the clock generator is configured so that the optical path length difference is equal to or larger than 32/n mm in air.

4. The imaging apparatus according to claim 1, further comprising:
a change unit provided on the second optical path to change the optical path length difference; and
a controller configured to control the change unit in accordance with the scan angle.

5. The imaging apparatus according to claim 1, further comprising:
a change unit provided on the second optical path to change the optical path length difference; and a controller configured to control the scan unit so as to change the scan angle in accordance with the selected image capture mode, and to control the change unit, and the processor further comprising a selection unit configured to select an image capture mode from among a plurality of image capture modes including three image capture modes in which an image of at least one of a macula and an optic disc of the fundus is captured.

6. The imaging apparatus according to claim 1, wherein the scan unit is configured so that the scan angle is changeable within a range from a first angle to a second angle, the first angle being equal to or larger than 47 degrees in air, the second angle being smaller than 47 degrees in air, and the clock generator is configured so that the optical path length difference is changeable within a range from a first optical path length difference to a second optical path length difference, the first optical path length difference being equal to or larger than 22/n mm in air, the second optical path length difference being smaller than 22/n mm in air.

7. The imaging apparatus according to claim 1, wherein the second optical path in the clock generator is configured by using a single path.

8. The imaging apparatus according to claim 1, wherein the clock generator is configured so that the frequency of the interferometer is converted into an integer multiple of the frequency of the interferometer, the integer multiple being equal to or larger than 2, the converted frequency being used as the frequency of the generated clock.

9. An imaging apparatus comprising:

a light source configured to emit light while sweeping a wavelength of the light;

an interference unit configured to split the light emitted from the light source into illumination light that is incident on a fundus and reference light and to generate interference light obtained by reflection light reflected from the fundus on which the illumination light is incident interfering with the reference light;

a scan unit configured to scan the illumination light across the fundus;

a detector configured to detect the interference light generated by the interference unit;

a converter configured to convert an analog signal generated from the interference light detected by the detector into a digital signal;

a clock generator configured as an interferometer including an optical path through which part of the light emitted from the light source passes, the optical path being split into a first optical path and a second optical path having an optical path length difference relative to the first optical path, to generate a clock used by the converter sampling the analog signal; and a processor including a tomographic image obtaining unit configured to obtain a tomographic image of the fundus by using the digital signal converted from the analog signal sampled by the converter in accordance with the generated clock, wherein the scan unit is configured to scan the illumination light across the fundus over a scan angle equal to or larger than 47 degrees in air, the tomographic image obtaining unit is configured to obtain a tomographic image of the fundus at a distance equal to or larger than 4.0 mm within an eyeball in a depth range, the second optical path in the clock generator is configured by using a double path, and the clock generator is configured so that the optical path length difference is equal to or larger than 11/n mm in air in a case where the generated clock has a frequency n times a frequency of the interferometer corresponding to the optical path length difference, n being an integer equal to or larger than 1.

10. The imaging apparatus according to claim 9, wherein the tomographic image obtaining unit is configured to obtain a tomographic image of the fundus at a distance equal to or larger than 5.0 mm within the eyeball in the depth range, and the clock generator is configured so that the optical path length difference is equal to or larger than 13.8/n mm in air.

11. The imaging apparatus according to claim 10, wherein the tomographic image obtaining unit is configured to obtain a tomographic image of the fundus at a distance equal to or larger than 5.8 mm within the eyeball in the depth range, and the clock generator is configured so that the optical path length difference is equal to or larger than 16/n mm in air.

12. An imaging apparatus comprising:

a light source configured to emit light while sweeping a wavelength of the light;

an interference unit configured to split the light emitted from the light source into illumination light that is incident on a fundus and reference light and to generate interference light obtained by reflection light reflected from the fundus on which the illumination light is incident interfering with the reference light;

a scan unit configured to scan the illumination light across the fundus;

a detector configured to detect the interference light generated by the interference unit;

a converter configured to convert an analog signal generated from the interference light detected by the detector into a digital signal;

a clock generator configured as an interferometer including an optical path through which part of the light emitted from the light source passes, the optical path being split into a first optical path and a second optical path having an optical path length difference relative to the first optical path, to generate a clock used by the converter sampling the analog signal; and a processor comprising a tomographic image obtaining unit configured to obtain a tomographic image of the fundus by using the digital signal converted from the analog signal sampled by the converter in accordance with the generated clock, wherein the scan unit is configured to scan the illumination light across the fundus over a scan angle equal to or larger than 47 degrees in air, and the tomographic image obtaining unit is configured to obtain a tomographic image of the fundus at a distance equal to or larger than 4.0 mm within an eyeball in a depth range.

13. The imaging apparatus according to claim 12, further comprising:

a change unit provided on the second optical path to change the optical path length difference; and a controller configured to control the change unit in accordance with the selected distance, and the processor further comprising a selection unit configured to select a distance of the tomographic image in the depth range.

14. The imaging apparatus according to claim 12, further comprising:
a change unit provided on the second optical path to change the optical path length difference; and
a controller configured to control the change unit in accordance with the selected image capture mode, and
the processor further comprising a selection unit configured to select an image capture mode from among a plurality of image capture modes including an image capture mode in which an image is captured so as to include a vitreous body, a retina, and a choroid.

15. The imaging apparatus according to claim 14, wherein the selection unit is configured to be able to select the distance within a range from a first distance to a second distance, the first distance being equal to or larger than 4.0 mm within the eyeball, the second distance being smaller than 4.0 mm within the eyeball, and
the clock generator is configured so that the optical path length difference is changeable within a range from a first optical path length difference to a second optical path length difference, the first optical path length difference being equal to or larger than a length corresponding to the distance equal to or larger than 4.0 mm within the eyeball, the second optical path length difference being smaller than the length corresponding to the distance equal to or larger than 4.0 mm within the eyeball.

16. The imaging apparatus according to claim 12, wherein the scan unit is configured to scan the illumination light across the fundus over a range of 14 mm or larger.

17. An imaging apparatus comprising:
a light source configured to emit light while sweeping a wavelength of the light;
an interference unit configured to split the light emitted from the light source into illumination light that is incident on a fundus and reference light and to generate interference light obtained by reflection light reflected from the fundus on which the illumination light is incident interfering with the reference light;
a detector configured to detect the interference light generated by the interference unit;
a scan unit configured to scan the illumination light across the fundus;
a converter configured to convert an analog signal generated from the interference light detected by the detector into a digital signal;
a clock generator configured to generate a clock used by the converter sampling the analog signal; and
a processor comprising a tomographic image obtaining unit configured to obtain a tomographic image of the fundus by using the digital signal converted from the analog signal sampled by the converter in accordance with the generated clock, wherein
the scan unit is configured to scan the illumination light across the fundus over a scan angle equal to or larger than 47 degrees in air,
the tomographic image obtaining unit is configured to obtain a tomographic image of the fundus at a distance equal to or larger than 4.0 mm within an eyeball in a depth range, and
the clock generator is configured so that the number of times the sampling is performed in a single sampling operation over the depth range of the tomographic image is equal to or larger than 2200.

18. The imaging apparatus according to claim 17, wherein the tomographic image obtaining unit is configured to obtain a tomographic image of the fundus at a distance equal to or larger than 5.0 mm within the eyeball in the depth range, and
the clock generator is configured so that the number of times the sampling is performed in a single sampling operation over the depth range of the tomographic image is equal to or larger than 2800.

19. The imaging apparatus according to claim 18, wherein the tomographic image obtaining unit is configured to obtain a tomographic image of the fundus at a distance equal to or larger than 5.8 mm within the eyeball in the depth range, and
the clock generator is configured so that the number of times the sampling is performed in a single sampling operation over the depth range of the tomographic image is equal to or larger than 3200.

20. An imaging apparatus comprising:
a light source configured to emit light while sweeping a wavelength of the light;
an interference unit configured to split the light emitted from the light source into illumination light that is incident on a fundus and reference light and to generate interference light obtained by reflection light reflected from the fundus on which the illumination light is incident interfering with the reference light;
a scan unit configured to scan the illumination light across the fundus;
a detector configured to detect the interference light generated by the interference unit;
a converter configured to convert an analog signal generated from the interference light detected by the detector into a digital signal;
a clock generator configured to generate a clock used by the converter sampling the analog signal; and
a processor comprising a tomographic image obtaining unit configured to obtain a tomographic image of the fundus by using the digital signal converted from the analog signal sampled by the converter in accordance with the generated clock, wherein
the scan unit is configured to scan the illumination light across the fundus over a scan angle equal to or larger than 47 degrees in air,
the tomographic image obtaining unit is configured to obtain a tomographic image of the fundus at a distance equal to or larger than 4.0 mm within an eyeball in a depth range, and
the clock generator is configured so that the clock has a frequency equal to or larger than 500 MHz.

21. The imaging apparatus according to claim 20, wherein the tomographic image obtaining unit is configured to obtain a tomographic image of the fundus at a distance equal to or larger than 5.0 mm within the eyeball in the depth range, and
the clock generator is configured so that the clock has a frequency equal to or larger than 620 MHz.

22. The imaging apparatus according to claim 21, wherein the tomographic image obtaining unit is configured to obtain a tomographic image of the fundus at a distance equal to or larger than 5.8 mm within the eyeball in the depth range, and
the clock generator is configured so that the clock has a frequency equal to or larger than 720 MHz.

23. An imaging apparatus comprising:
- a light source configured to emit light while sweeping a wavelength of the light;
- an interference unit configured to split the light emitted from the light source into illumination light that is incident on a fundus and reference light and to generate interference light obtained by reflection light reflected from the fundus on which the illumination light is incident interfering with the reference light;
- a detector configured to detect the interference light generated by the interference unit;
- a converter configured to convert an analog signal generated from the interference light detected by the detector into a digital signal;
- a clock generator configured to generate a clock used by the converter sampling the analog signal; and
- a processor comprising a tomographic image obtaining unit configured to obtain a tomographic image of the fundus by using the digital signal converted from the analog signal sampled by the converter in accordance with the generated clock, wherein
- the tomographic image obtaining unit is configured to obtain a tomographic image of the fundus at a distance equal to or larger than 4.0 mm within an eyeball in a depth range, and
- the clock generator is configured to generate the clock having a frequency that corresponds to the distance equal to or larger than 4.0 mm within the eyeball.

24. The imaging apparatus according to claim 23, further comprising:
- a scan unit configured to scan the illumination light across the fundus, wherein
- the scan unit is configured to scan the illumination light across the fundus over a scan angle equal to or larger than 47 degrees in air.

25. The imaging apparatus according to claim 23, wherein the light source is a surface-emitting laser that includes a lower reflection mirror, an active layer, and an upper reflection mirror in this order, has a cavity between the active layer and the upper reflection mirror, and changes a position of at least one of the upper reflection mirror and the lower reflection mirror in an optical axis direction to change the wavelength of the emitted light.

26. The imaging apparatus according to claim 23, wherein the tomographic image obtaining unit is configured to obtain tomographic data of the fundus at the distance equal to or larger than 4.0 mm within the eyeball in the depth range and to generate a new tomographic image by removing, from the obtained tomographic data, part of the obtained tomographic data corresponding to part of the depth range.

27. The imaging apparatus according to claim 23, wherein the processor further comprising:
- an analysis unit configured to analyze the obtained tomographic image to perform segmentation into a plurality of layers;
- an image generation unit configured to generate a planar image along any of the plurality of layers in accordance with an analysis result from the analysis unit; and
- a display controller configured to display the planar image and the tomographic image on a display while positions of a macula and an optic disc of the fundus which are included in the planar image are associated with positions of the macula and the optic disc of the fundus which are included in the tomographic image.

28. The imaging apparatus according to claim 23, wherein the clock generator generates the clock so that the converter samples the analog signal at substantially equal wavenumber intervals.

* * * * *